(12) United States Patent
Mortazavi

(10) Patent No.: US 8,789,727 B2
(45) Date of Patent: Jul. 29, 2014

(54) INDUCTIVELY OPERATED FLUID DISPENSING DEVICE

(75) Inventor: Behzad Mortazavi, Pully (CH)

(73) Assignee: Alpimed Sarl, Pully (CH)

( * ) Notice: Subject to any disclaimer, the term of this patent is extended or adjusted under 35 U.S.C. 154(b) by 6 days.

(21) Appl. No.: 13/598,235

(22) Filed: Aug. 29, 2012

(65) Prior Publication Data

US 2013/0037578 A1 Feb. 14, 2013

Related U.S. Application Data

(63) Continuation of application No. PCT/EP2010/054445, filed on Apr. 1, 2010.

(51) Int. Cl.
*B65D 88/54* (2006.01)

(52) U.S. Cl.
USPC ............ 222/327; 222/1; 222/333; 222/386

(58) Field of Classification Search
USPC ........ 222/325, 326, 333, 386, 1, 327; 433/89, 433/98, 99; 604/67, 152, 164.01, 207, 232, 604/235; 417/44.1, 53, 419
See application file for complete search history.

(56) References Cited

U.S. PATENT DOCUMENTS

| | | | | |
|---|---|---|---|---|
| 4,067,481 A | * | 1/1978 | Feldman | 222/146.5 |
| 5,188,259 A | * | 2/1993 | Petit | 222/63 |
| 6,068,615 A | * | 5/2000 | Brown et al. | 604/207 |
| 2006/0258986 A1 | | 11/2006 | Hunter et al. | |
| 2007/0129681 A1 | | 6/2007 | Ott | |
| 2008/0135583 A1 | * | 6/2008 | Caswell et al. | 222/333 |
| 2008/0294098 A1 | | 11/2008 | Sarkinen et al. | |
| 2009/0043253 A1 | * | 2/2009 | Podaima | 604/67 |
| 2009/0097995 A1 | | 4/2009 | Ham et al. | |
| 2009/0105650 A1 | | 4/2009 | Wiegel et al. | |
| 2010/0211003 A1 | * | 8/2010 | Sundar et al. | 604/67 |
| 2012/0059349 A1 | * | 3/2012 | Kuo et al. | 604/500 |
| 2012/0238999 A1 | * | 9/2012 | Estes et al. | 604/504 |
| 2013/0172810 A1 | * | 7/2013 | Steinbach | 604/67 |
| 2013/0231608 A1 | * | 9/2013 | Kamen et al. | 604/67 |

FOREIGN PATENT DOCUMENTS

| | | |
|---|---|---|
| EP | 2065064 A1 | 6/2009 |
| WO | WO-03023226 A1 | 3/2003 |
| WO | WO-0310376 A1 | 12/2003 |
| WO | WO-2008003625 A1 | 1/2008 |
| WO | WO-2008027579 A1 | 3/2008 |

* cited by examiner

*Primary Examiner* — Kevin P Shaver
*Assistant Examiner* — Patrick M Buechner
(74) *Attorney, Agent, or Firm* — Blank Rome LLP

(57) ABSTRACT

A device for delivering fluid, having an elongated outer casing (10) provided with a substantially cylindrical inner chamber (11); an inner cartridge (20), for insertion into the inner chamber (11) and including a plunger (21) movable axially along a longitudinal axis A-A of an inner reservoir (22) towards an outlet (28). The device also includes a coil assembly (12, 23, 24) having an outer coil (12), an inner coil (23) and an inner coil core (24). The outer coil (12) is provided on the outer casing (10) and axially oriented along the chamber longitudinal axis. And, the inner coil (23) is provided in the inner cartridge (20) attached to the movable plunger (21).

11 Claims, 1 Drawing Sheet

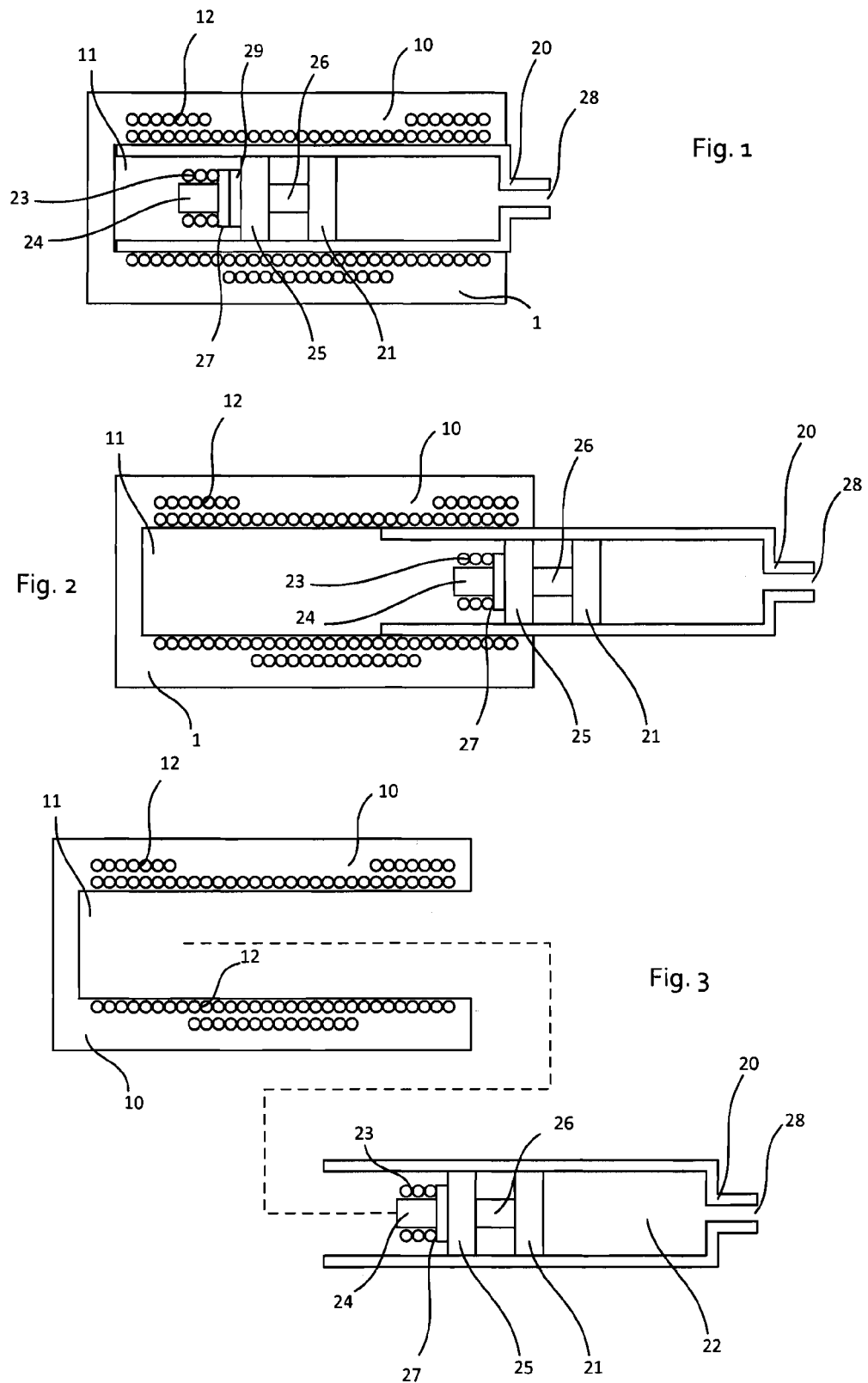

INDUCTIVELY OPERATED FLUID DISPENSING DEVICE

REFERENCE DATA

The present application is a continuation of international patent application PCT/EP2010/054445 filed on 1 Apr. 2010, the entire contents of which is hereby incorporated by reference.

FIELD OF THE INVENTION

The present invention relates to a device for delivering fluid, comprising an elongated outer casing provided with a substantially cylindrical inner chamber, and an inner cartridge for insertion into said inner chamber. The cartridge comprises a plunger movable axially along a longitudinal axis of an inner reservoir towards an outlet. The device also comprises a coil assembly. The invention also relates to the corresponding method for delivering fluid from a cartridge.

Some embodiments of the present invention relate to a device for administering pharmaceutical drugs by injection or infusion, yet the invention is not limited to this application and could also serve to deliver precisely metered amounts of adhesives, lubricants, solder pastes, chemical reagents, or any other fluid in all suitable industrial applications.

BACKGROUND OF THE INVENTION

Several pharmaceutical drugs are preferably or exclusively delivered by infusion or injection, traditionally by a hand-operated syringe equipped with a hypodermic needle. Though effective, this method is a source of discomfort for patients requiring repeated injections over an extended period, for example diabetes patients. Moreover a number of patients, in particularly elderly, visual-impaired, or patients suffering from arthritis, do not have the manual dexterity required to self-administer a hypodermic injection.

In some cases like dental injections in the gums, the injections discomfort and pain can be attenuated if the drug is delivered at a constant and moderate rate. Unfortunately this is not always possible, even with the best injection technique.

It is also known to employ special syringes, also termed "insulin pens", adapted to deliver a precisely metered dose of drug through a fine-gauge needle, by the action of a piston operated by a press button. These pens are easier to use than conventional syringes, yet they still require a certain amount of dexterity and force, and some patients find their use difficult.

It is also known to use motorized infusion pumps when there is a indication to deliver a drug at a constant low rate protracted along an extended period.

US 2009105650 describes a drug delivery pump drive which uses a linear piezoelectric motor to advance a syringe piston to deliver a liquid drug. The pump drive, provided in a drug delivery pump, provides silent operation and very low energy consumption compared to electric motor-based drives.

US 2009097995 describes a syringe pump which uses the linear actuator applying a linear motion of a piezoelectric linear motor in moving the piston, such that suction and exhaustion of the fluid can be performed more precisely through controlling of power supply with respect to the piezoelectric linear motor. The syringe pump includes a cylinder which includes a receiving space, a piston which is mounted in the cylinder to pump liquid or powder in and out of the cylinder, and a piezoelectric linear actuator which moves the piston in a reciprocating manner. In addition, the piezoelectric linear actuator comprises a piezoelectric linear motor.

WO 03103763 describes a device for delivering fluid, such as insulin, to a patient. The device includes an exit port assembly, a syringe-like reservoir including a side wall extending along a longitudinal axis towards an outlet connected to the exit port assembly, and a plunger assembly received in the reservoir. Successively actuating the actuator causes longitudinal movement of the plunger assembly towards the outlet of the reservoir in order to dispense the fluid. According to one exemplary embodiment, the actuator comprises an elongated shape memory element. In a further embodiment, the actuator comprises a solenoid assembly.

US2007129681 describes a fluid dispenser having a housing for defining a fluid chamber. The housing has an orifice through which fluid is discharged. A piston is positioned in the housing for linear motion in the chamber for expelling fluid from the chamber and through the orifice. A piezoelectric actuator assembly is positioned in the housing for imparting the linear motion to the piston. In one example implementation, the fluid dispenser housing takes the form of a syringe. In the syringe implementation, a syringe housing defines an essentially cylindrical fluid chamber. In an example embodiment, the piezoelectric actuator assembly comprises a first piezoelectric actuator; a second piezoelectric actuator; and, a circuit for actuating the first piezoelectric actuator and the second piezoelectric actuator.

WO2008/003625 discloses an automatic infusion or injection device in which the amount and type of the drug contained in a cartridge is determined inductively.

All these embodiments involve complex electrical connections in order to provide power to the fluid delivery actuator. Moreover, feedback about the proper operation of the system, about status, etc, is not provided. Single part products comprising the fluid reservoir and the actuation means a higher costs product.

SUMMARY OF THE INVENTION

A general aim of the invention is therefore to provide an improved fluid delivery device with easily detachable cartridge portion.

A further aim of the invention is to provide such fluid delivery device, which offers more possibilities for controlling status of fluid delivery, detect the position of the plunger, detect any blockage or obstruction, control fluid type, etc.

Still another aim of the invention is to provide a device offering more precision in fluid delivery and that is simpler and easier to use than conventional injection devices.

Yet another aim of the invention is to provide such fluid delivery device, requiring less power resources.

These aims are achieved thanks to the fluid delivery device and fluid delivery method defined in the claims.

There is accordingly provided a device for delivering fluid, comprising:
- an elongated outer casing provided with a substantially cylindrical inner chamber;
- an inner cartridge, for insertion into said inner chamber and comprising a plunger movable axially along a longitudinal axis A-A of an inner reservoir towards an outlet;
- a coil assembly comprising an outer coil, an inner coil and an inner coil core;
- said outer coil is provided on said outer casing and axially oriented along the chamber longitudinal axis and;
- said inner coil is provided in said inner cartridge attached to said movable plunger.

The device is advantageously provided with two main components, that is to say the outer casing and the inner cartridge. This enables an optimized use for each of these components as well as a quick and easy interchangeability of the cartridge. By placing the moving parts in the disposable cartridge, one removes the difficulty and the need of calibration and recalibration of the moving part after a given period. The outer casing contains no moving parts and therefore can be made extremely robust, miniaturized, at low cost.

Such an arrangement enables to spread the cost of the units over the period of usage and does not require a high investment at the beginning. This also substantially reduces the entry cost barrier for new users.

In a preferred embodiment, the coil assembly is adapted for power transmission from outer coil to inner coil of inner cartridge.

Except the sliding movement of the cartridge into the outer casing, there is no mechanical or electrical connection between the cartridge and the outer casing. The inductive coupling between the cartridge and the outer casing considerably simplifies the insertion and removal of the cartridge inside the casing.

In an advantageous embodiment, the movable plunger comprises an actuation device for providing axial displacement of plunger in said reservoir, said actuation device being connected to said inner coil. The inner coil preferably comprises an inner coil core, around which said inner coil is spirally arranged.

In a preferred embodiment, the actuation device comprises a piezoelectric actuator configured to produce linear motion of the plunger. The piezoelectric movement assembly requires less energy than a conventional motor and therefore requires a smaller battery in the base unit.

The outer casing advantageously comprises an access to a power input, for instance a battery on said outer casing or a connector for connection to an outer power source.

The coil assembly is advantageously operable as a data transfer unit for data transfer between inner cartridge and outer casing.

The cartridge advantageously contains information that allows the protection of the user and prevents errors such as injection of a wrong medication or injection of a high concentration medication instead of a low concentration medication. In a further variant, involving more automated components, the outer casing dynamically and automatically adjusts its injection profile to the medication in the cartridge.

In an advantageous embodiment, data transfer is operable at least from inner cartridge towards outer casing. In a variant, it is bidirectional.

In a variant, the coil assembly is operable as a Linear Variable Differential Transformer (LVDT), for indicating the axial position of said plunger along the reservoir.

When the inner cartridge is inserted into the corresponding outer casing, the longitudinal axis A-A of the cartridge reservoir and the longitudinal axis of the chamber are preferably the same, or are in correspondence.

The invention also provides a method for delivering fluid from a cartridge, comprising:
  providing an elongated outer casing having a substantially cylindrical inner chamber;
  providing an inner cartridge, for insertion into said inner chamber and comprising a plunger movable axially along a longitudinal axis A-A of an inner reservoir;
  providing a coil assembly, such that;
  at least one outer coil is provided on said outer casing and axially oriented along the chamber longitudinal axis and;
  at least one inner coil is provided in said inner cartridge attached to said movable plunger.

In an advantageous embodiment, power transmission from outer coil to inner coil of inner cartridge is used for providing power to an actuation device thereby allowing axial displacement of plunger in said reservoir.

In a further embodiment, the coil assembly is operable as a data transfer unit for data transfer between inner cartridge and outer casing. Data transfer between inner cartridge and outer casing is advantageously used for sending status or operation data from said cartridge to outer casing. It may also be used to assist an automated operation of the device.

Advantageously, the coil assembly is operable as a Linear Variable Differential Transformer (LVDT), for indicating the axial position of said plunger along the reservoir.

BRIEF DESCRIPTION OF THE DRAWINGS

The foregoing and other purposes, features, aspects and advantages of the invention will become apparent from the following detailed description of embodiments, given by way of illustration and not limitation with reference to the accompanying drawings, in which:

FIG. 1 is a schematic diagram showing the structure of a device for delivering fluid in accordance with the invention;

FIG. 2 is a schematic diagram showing the device of FIG. 1, the cartridge being partially out of the outer casing;

FIG. 3 is a schematic diagram showing the device of FIG. 1, the cartridge being fully removed from the outer casing.

DETAILED DESCRIPTION OF THE INVENTION

Referring to FIG. 1, the device 1 for delivering fluid comprises two main components: an outer casing 10, and an inner cartridge 20. The cartridge is preferably removable from the casing 10. In a preferred embodiment, the cartridge is a syringe, usable for instance to provide insulin or any other medication or drug to a patient.

The outer casing 10 is provided with a substantially cylindrical chamber 11, with an open end, for placement and removal of the cartridge and to provide the required space for an outlet 28 as described hereafter.

At least one outer coil 12 is spirally provided in the casing in order to surround the chamber 11. In variants, a plurality of outer coils are provided, with different configurations, depending on the overall dimensions of the device and the required performances.

The inner cartridge 20 comprises an elongated cylindrical reservoir 22 for containing the fluid to be delivered. An outlet 28 provided at one end thereof enables the fluid to flow out of the reservoir upon actuation of a plunger 21. This plunger is axially movable along the reservoir and also closes the reservoir end opposed to the outlet. The outlet 28 is used for connection of tubes allowing transporting the fluid to the dispensing point. It may also be connected to a needle or other type of medical interface with a patient.

A piezoelectric actuator 25 provides actuation of the plunger 21, in a known manner. The piezoelectric linear actuator comprises a piezoelectric linear motor performing a linear motion. In a preferred variant, the actuation device may comprise an ultrasonic type piezoelectric actuator. Low power consumption, minimized required space, high precision and high reliability are the main advantages of the piezoelectric technology. Other actuators could also be used, in replacement to the piezoelectric motor, for example a shape-memory motor, a linear electric motor, or any other suitable linear actuator.

In some embodiments, the cartridge includes at least one inner coil 23 and/or a Printed Circuit Board (PCB) assembly 27 containing the driving electronics circuit is placed between the piezoelectric actuator 25 and the coil 23/core 24 arrangement. The PCB may also include memory elements used for storing the cartridge data. A piezo-plunger coupling 26 may also provided to connect or attach the plunger 21 and the piezoelectric actuator 25. Preferably the inner coil 23 is wound on a core 24, for example a ferromagnetic core, in order to increase the magnetic coupling and optimize the energy transfer. In some variant, however, the inner coil or coils 23 could be wound without a core.

In FIG. 1, the inner cartridge 20 in fully inserted into the outer casing 10.

FIG. 2 shows the same device 1 as in FIG. 1, but with the cartridge 20 partially extracted from the outer casing 10.

FIG. 3 depicts the same device 1 with its two main components fully separated once the cartridge 20 is entirely extracted from the outer casing 10.

The illustrated device 1 is adapted to operate according to different possibilities, as described hereafter.

Case 1: Outer Coil to Inner Coil Power Transfer

The outer coil 12 inductively transfers power to the inner coil 23, which energizes the piezoelectric actuator 25. The coil assembly, provided with outer coil 12 and inner coil 23, provides a transformer allowing the required voltage increase to drive the piezoelectric elements. When the proper signal sequence on the outer coil is provided, a linear stepwise movement of the piezoelectric actuator is generated, thereby causing a linear stepwise movement of the plunger 21.

Case 2: Outer Coil to Inner Coil Actuation Commands Transmission

According to this embodiment, the cartridge includes an energy source 29, for example an electrochemical battery or an accumulator. External coil 12 is used to transmit inductively actuation commands to the actuator 25 through the inner coil 23. For example, the actuator could receive inductively commands to start or stop motion of the plunger at a given speed, or to advance or retract the plunger by a given number of steps, or by a given distance, according to the implementation. In a variant, the energy source may be a rechargeable accumulator or a capacitor that can be recharged inductively by coils 12 and 23, for example during the periods of inactivity of the device. For simplicity's sake the energy source 29 is represented in FIG. 1 only.

Case 3: Inner Coil—Outer Coil Bidirectional or Unidirectional Data Transfer

The PCB electronics 27 contains a data transfer circuit, such as RFID circuit, allowing data transfer to the outer coil 12. The cartridge data may be contained in specific data storage element or within the piezoelectric driving or controlling electronics 27. Data may be static non-erasable data written during manufacturing, such as the medication details, expiry date, concentration, maximum daily dosage, manufacturer data, exact injection volume at each step, and the like. The transferred data can also be related to the movement of the piezoelectric assembly such as the discharge and charge times of the piezoelectric elements. Such movement indication gives information about the smoothness of the movement, which can be used to detect any blockage in the fluid path or the eventual formation of bubbles.

The use of the outer coil assembly as a data transfer interface constitutes an independent aspect of the invention that also allows embodiments in which the inner cartridge does not include a magnetic core, but simply a RFID antenna that can transfer data to and from the coil. The RFID antenna in the cartridge could be a coil, but this is not the only option.

Case 4: Outer Coil Detection of the Position of the Inner Coil

The outer coil allows a Linear Variable Differential Transformer (LVDT) setup using the ferromagnetic core 24 of the inner coil 23. This enables the outer coil 12 to receive data about the position of the inner coil. This information can be used to detect the liquid level, to detect an empty cartridge, etc. It also allows a monitoring of the proper axial displacement of the plunger. Any detection of an unexpected position of the plunger may be used to generate a warning or an error message. In an advantageous embodiment, the LVDT configuration is provided with three coils, that is to say one primary and two secondaries, the latter being preferably placed on the movable portion of the cartridge. A cylindrical ferromagnetic core, connected to the element whose position is to be measured, slides along the axis. In order to avoid having an inner core extending along two coils, a variant provides an arrangement in which the two inner coils (with their respective inner cores) are separated. For instance, a first coil is placed as shown in the example of FIG. 1, whereas the second one is placed between the plunger 21 and piezoelectric assembly 25.

The use of the outer coil assembly as LVDT constitutes an independent variant of the present invention which allows also embodiments lacking an inner coil. In this case the plunger simply incorporates a ferromagnetic core, in order to provide a suitable signal for the LVDT's secondary winding, and the advancement of the plunger is assured by some suitable mechanical, electric, hydraulic or pneumatic actuator.

The above detailed description with reference to the drawings illustrates rather than limit the invention. There are numerous alternatives, which fall within the scope of the appended claims. For instance, the device and method of the invention may be operated according to any one of the three above-mentioned cases, or any combination thereof. The coils used for RFID and/or the coils used for LVDT may be the same as the coils used for power transfer or specific coils for a specific use, without departing from the invention.

A preferred embodiment of the invention is a portable insulin pump, comprising a device as described above for delivering insulin in liquid form. Preferably the device can accept insulin cartridges including a piezoelectric actuator that advances a plunger in the cartridge, thus delivering a defined flow of the drug. The power supply to the piezoelectric actuator is transmitted inductively and contactlessly from a coil in the device to an inner coil in the cartridge. Preferably, the position of the plunger is also measured contactlessly by a LVDT-type encoder, and this measure is used to control the flow of drug. This invention ensures a more precise metering of insulin and/or a smaller size than the insulin infusion pumps known in the art.

Another embodiment of the invention is a motorized insulin pen comprising a device as described above and including an electrically operated plunger that can be used to deliver a single predetermined dose of insulin or of another drug. Advantageously, this embodiment of the invention is easier to use that known manually operated insulin pens. This embodiment of the invention could be realized both as a disposable device, to be discarded once its prefilled cartridge is empty, and as a durable device accepting replaceable insulin cartridges. The plunger is operated by a suitable actuator contained in the cartridge, for example a piezoelectric motor, which preferably receives a contactless power supply by an outer coil and an inner coil, as explained above. The determination of the plunger's position by a LVDT system is helpful to meter precisely the dose of drug delivered.

Although the figures represent the plunger 21, the inner coil 23, the plunger actuator 25, and the magnetic inner core 24 as separate and distinct, this is not a limitation of the invention. It is conceivable, rather, that some or all of these features could be integrated inside the plunger, dispensing of the coupling 26. This has the desirable outcome of increasing the active volume of the cartridge, without increasing the size of the infusion device.

The word "comprising" does not exclude the presence of other elements or steps than those listed in a claim. The word "a" or "an" preceding an element or step does not exclude the presence of a plurality of such elements or steps. The mere fact that respective dependent claims define respective additional features, does not exclude a combination of additional features, which corresponds to a combination of dependent claims.

The invention claimed is:

1. A device for delivering fluid, comprising:
   an elongated outer casing provided with a substantially cylindrical inner chamber;
   an inner cartridge, for insertion into said inner chamber and comprising a plunger movable axially along a longitudinal axis of an inner reservoir towards an outlet;
   a coil assembly comprising one or several outer coils, on said outer casing and axially oriented along the chamber longitudinal axis,
   wherein an inner coil in said inner cartridge is attached to said movable plunger and said coil assembly is adapted for power transmission from the outer coil to the inner coil of the inner cartridge.

2. A device for delivering fluid according to claim 1, further comprising an actuation device configured to provide axial displacement of said plunger in said reservoir.

3. A device for delivering fluid according to claim 2, wherein said actuation device comprises a piezoelectric actuator configured to produce linear motion of the plunger.

4. A device for delivering fluid according to claim 1, said inner coil further comprising an inner coil core, around which said inner coil is spirally arranged.

5. A device for delivering fluid according to claim 1, wherein said coil assembly is operable as a Linear Variable Differential Transformer (LVDT), for indicating the axial position of said plunger along the reservoir.

6. A device for delivering fluid according to claim 1, wherein when the inner cartridge is inserted into the corresponding outer casing, the longitudinal axis of the cartridge reservoir and the longitudinal axis of the chamber are the same.

7. A device for delivering fluid, comprising:
   an elongated outer casing provided with a substantially cylindrical inner chamber;
   an inner cartridge, for insertion into said inner chamber and comprising a plunger movable axially along a longitudinal axis of an inner reservoir towards an outlet;
   a coil assembly comprising one or several outer coils, on said outer casing and axially oriented along the chamber longitudinal axis, wherein said coil assembly is operable as a data transfer unit for data transfer between inner cartridge and outer casing, and
   wherein an inner coil in said inner cartridge is attached to said movable plunger.

8. A device for delivering fluid according to claim 7, wherein data transfer is operable at least from inner cartridge towards outer casing.

9. A method for delivering fluid from a cartridge, comprising the steps of:
   providing an elongated outer casing having a substantially cylindrical inner chamber;
   providing an inner cartridge, for insertion into said inner chamber and comprising a plunger movable axially along a longitudinal axis of an inner reservoir;
   providing a coil assembly, such that:
   at least one outer coil is provided on said outer casing and axially oriented along the chamber longitudinal axis, and an inner coil is provided in said inner cartridge attached to said movable plunger, wherein power transmission from the at least one outer coil to the inner coil of inner cartridge is used for providing power to an actuation device thereby allowing axial displacement of plunger in said reservoir.

10. A method for delivering fluid according to claim 9, wherein said coil assembly is operable as a data transfer unit for data transfer between inner cartridge and outer casing.

11. A method for delivering fluid according to claim 9, wherein said coil assembly is operable as a Linear Variable Differential Transformer (LVDT), for indicating the axial position of said plunger along the reservoir.

* * * * *